US008067471B2

(12) United States Patent
Whippie et al.

(10) Patent No.: US 8,067,471 B2
(45) Date of Patent: Nov. 29, 2011

(54) COMPOSITION COMPRISING FREE AMINO ACIDS

(75) Inventors: Constance Whippie, New Milford, CT (US); Olivier Ballevre, Lausanne (CH); Julio Boza, La Conversion-Lutry (CH); Paul-André Finot, St-Legier (CH)

(73) Assignee: Nestec S.A., Vevey (CH)

( * ) Notice: Subject to any disclaimer, the term of this patent is extended or adjusted under 35 U.S.C. 154(b) by 549 days.

(21) Appl. No.: 11/380,841

(22) Filed: Apr. 28, 2006

(65) Prior Publication Data

US 2006/0247312 A1 Nov. 2, 2006

Related U.S. Application Data

(63) Continuation of application No. 10/240,025, filed as application No. PCT/EP01/03188 on Mar. 21, 2001, now abandoned.

(30) Foreign Application Priority Data

Apr. 12, 2000 (GB) .................................. 0009056.3

(51) Int. Cl.
*A61K 31/195* (2006.01)
(52) U.S. Cl. ........................................ 514/561; 514/562
(58) Field of Classification Search ........................ None
See application file for complete search history.

(56) References Cited

U.S. PATENT DOCUMENTS

| 4,042,687 | A | | 8/1977 | Gans et al. |
| 4,053,589 | A | * | 10/1977 | Gans et al. ................. 514/21 |
| 4,414,238 | A | | 11/1983 | Schmidl |
| 5,106,836 | A | | 4/1992 | Clemens et al. |
| 5,438,042 | A | | 8/1995 | Schmidl et al. |
| 5,504,072 | A | | 4/1996 | Schmidl et al. |
| 5,719,133 | A | | 2/1998 | Schmidl et al. |

FOREIGN PATENT DOCUMENTS

| EP | 0148680 | | 12/1984 |
| EP | 0917826 | | 5/1989 |
| FR | 2154397 | | 5/1973 |
| GB | 2223925 | | 4/1990 |
| RU | 2080871 | * | 6/1997 |
| RU | 2091067 | * | 9/1997 |
| WO | WO9414458 | | 7/1994 |
| WO | WO9854985 | | 12/1998 |
| WO | WO99/13738 | | 3/1999 |

OTHER PUBLICATIONS

Biochemistry—a functional approach (McGilvery), p. 362, (1970).*
Maxvold et al., Critical Care Medicine, 28(4), pp. 1161-1165, (Nov. 2000).*
Foitzik et al., International journal of colorectal disease, (1999) 14(3), pp. 143-149.*
Zhang et al., Shandong Yike Daxue Xuebao (2001), 39(6), 531-533 (abstract).*
"The Merck Manual of Diagnosis and Therapy," Seventeenth Edition (1999) Chapter 30—Malabsorption Syndromes pp. 301-303.

* cited by examiner

*Primary Examiner* — Phyllis G. Spivack
(74) *Attorney, Agent, or Firm* — K&L Gates LLP

(57) ABSTRACT

A composition is described that can be used in prevention or treatment of patients having impaired gastro-intestinal tract function. The composition comprises free amino acids including about 9.0% to about 17.0% glutamic acid. Methods of treatment of impaired gastro-intestinal tract function are described.

15 Claims, No Drawings

COMPOSITION COMPRISING FREE AMINO ACIDS

PRIORITY CLAIM

This application is a continuation of U.S. patent application Ser. No. 10/240,025 filed on Jan. 2, 2003, now abandoned, which is a U.S. national stage application of PCT/EP01/03188 filed on Mar. 21, 2001, the entire disclosures of which are hereby incorporated.

DETAILED DESCRIPTION

The present invention relates to a composition comprising free amino acids, a method of production of the composition, use of the composition in the manufacture of a medicament for the prevention or treatment of impaired gastro-intestinal tract function, and a method of treatment of impaired gastro-intestinal tract function which comprises administering an effective amount of the composition.

Within the context of this specification the word "comprises" is taken to mean "includes, among other things". It is not intended to be construed as "consists of only". DNA bases and amino acids are represented herein by their standard one or three letter abbreviations as defined by the IUPAC-IUB Biochemical Nomenclature Commission. GI is used as an abbreviation for gastro-intestinal.

Within the context of this specification the term "impaired gastro-intestinal tract function" represents all ailments wherein the GI tract is compromised including inflammatory bowel conditions and other ailments selected from patients suffering from surgery, trauma, burns, malnutrition, chronic illness or those suffering from prolonged periods of reduced oral intake.

Patients suffering from a loss of nutrients require adequate nutritional support. A lack of adequate nutritional support can result in malnutrition associated complications. Thus, the goal of nutritional support is to maintain body mass, provide nitrogen and energy in adequate amounts to support healing, meet metabolic demands characterised by the degree of stress, and support immune function.

A traditional form of nutritional support has involved enterally administering whole protein liquid formula to a patient to remedy protein deficiency. However, some patients requiring nutritional support have a compromised absorptive capacity and thus cannot tolerate whole protein liquid formulae as well as the long-chain fatty acids or complex carbohydrates often present in such whole protein formulae.

It is known that many diseases and/or their consequences can give rise to malabsorption of dietary nutrients by impairment of either digestion and/or absorption. For instance, patients suffering from various types of inflammatory bowel disease typically cannot tolerate whole protein formulae. As a result, enteral formulae have been developed to treat such compromised patients such as those disclosed in U.S. Pat. No. 5,438,042, U.S. Pat. No. 5,504,072 or U.S. Pat. No. 5,719,133 (all in the name of Schmidl et al).

As well as patients suffering from inflammatory bowel disease, patients suffering from other conditions may be treated with enteral formulae. They include, for example, total parenteral nutrition patients receiving early transitional formulae, acutely ill, and catabolic patients. Patients suffering from surgery, trauma, burns, malnutrition, chronic illness or those suffering from prolonged periods of reduced oral intake may also require treatment.

However, the known formulae do not adequately meet the metabolic needs of such patients.

In addition, the known formulae suffer from the problems that they are unstable having a shelf life under refrigeration of no more than 48 hours. This means that either they can not be stored in a form that is ready to use or that after a short period the known formulae must be disposed of because they have reached the end of their shelf life. Of course, this is not an efficient use of resources.

Therefore, a need exists for an enteral or oral nutritional composition that meets the nutrient requirements of metabolically stressed patients. Furthermore, there is a need for a composition which is stable and can be stored in a ready to use form until required.

The present invention addresses the problems set out above.

Remarkably, a composition has now been found that may be administered to patients suffering from impaired gastrointestinal tract function. In addition, it has now surprisingly been found that this composition is capable of being stored in a form that is ready to use and has a shelf life of at least nine months (and more likely in the region of a complete year) in its intact container.

Accordingly, in a first aspect the present invention provides a composition for the treatment of impaired gastrointestinal tract function which comprises free amino acids including about 9.0% to about 17.0% glutamic acid by weight of total amino acid composition.

In a second aspect the invention provides a method of producing the composition which comprises the steps of blending free amino acids including about 9.0% to about 17.0% glutamic acid by weight of total amino acid composition with a carrier diluent or excipient.

In a third aspect the invention provides use of the composition in the manufacture of a medicament for the treatment of impaired gastro-intestinal tract function.

In a forth aspect the invention provides a method of treatment of impaired gastrointestinal tract function which comprises administering an effective amount of the composition.

Advantageously, an embodiment of a composition according to the invention is remarkably stable having a shelf life of at least nine months and more likely in the region of a complete year in its intact container.

Advantageously, an embodiment of a composition according to the invention corresponds closely with the amino acid requirement and body protein distribution of a human or companion animal.

Preferably an embodiment of the composition is in ready to use form for use in providing oral or enteral nutrition.

Preferably, no glutamine is added. In direct contrast to known formulae, which have added glutamine, this amino acid is preferably substantially absent in an embodiment of the present invention. In view of the fact that this amino acid is not heat stable it provides the advantage that an embodiment of the composition can be treated with heat during its preparation.

Preferably arginine is present, but in contrast to known formulae the level of this amino acid is not high. This provides the advantage that a low level of arginine in a diet promotes plasma and muscle glutamine levels. A low level of arginine (eg about 3% total amino acids by weight) compared to known formulae (eg about 11.1% total amino acids by weight) stimulates the endogenous production of glutamine. Furthermore, arginine and glutamine are rich in nitrogen which must be detoxified and excreted in urea. This is energy consuming and can contribute to overloading of the kidneys.

Preferably an embodiment of the composition comprises a high level of amino acids comprising sulphur. Preferably an embodiment of the composition comprises cysteine. A high level of methionine or cysteine contributes to an increase in the bioavailability of cysteine for its specific roles. This provides the advantage that cysteine promotes recovery or resistance to an acute inflammatory condition.

Preferably an embodiment of the composition comprises aspartic acid. This provides the advantage that aspartic acid promotes recovery or resistance to an acute inflammatory condition.

Preferably an embodiment of the composition comprises leucine. This provides the advantage that leucine promotes stimulation of muscle protein synthesis.

Preferably an embodiment of the composition comprises threonine. This provides the advantage that it meets the increased requirement for this amino acid during acute inflammation and hypercatabolism for synthesis of inflammatory proteins. In addition a high level of this amino acid helps reduce muscle protein breakdown and spare muscle mass.

Preferably an embodiment of the composition comprises proline. This provides the advantage that proline promotes synthesis of collagen and thereby promotes wound healing.

Preferably an embodiment of the composition comprises tryptophan. This provides the advantage that tryptophan promotes an increase of protein synthesis.

Preferably an embodiment of the composition comprises serine. This provides the advantage that it meets the increased requirement for this amino acid during acute inflammation and hypercatabolism for synthesis of inflammatory proteins.

Preferably an embodiment of the composition comprises cysteine. This provides the advantages that it is a direct precursor of glutathione which is a scavenger of the free radicals produced during acute inflammation, sepsis, hypercatabolism, ischemia, etc. In addition, it promotes an increase in the redox potential of the body and promotes synthesis of inflammatory proteins which are rich in this amino acid.

Preferably an embodiment of the composition comprises lysine.

Preferably an embodiment of the composition comprises branched amino acids. This provides the advantage that it they are required for maintenance of muscle mass and increased glutamine status.

Advantageously, the overall amino acid profile of an embodiment of a composition according to the invention is suitable for nutrition of an intensive care patient.

Advantageously, in alternative embodiments of the invention some amino acids may be provided in the form of short polypeptides of as acyl-derivatives. This provides the advantage of improving their solubility (tyrosine, cysteine, glutamine) or increasing their stability to heat treatment (cysteine and glutamine). Alternatively, cysteine may be provided in the form of cystine.

Preferably, an embodiment of the composition according to the present invention comprises one or more of the following amino acids in the following amounts:

| Amino Acids | Amount (g/100 g total amino acids) |
|---|---|
| Ile | 5.7-7.0 |
| Leu | 10.8-14.0 |
| Lys | 6.5-10.0 |
| Met | 2.4-3.2 |

-continued

| Amino Acids | Amount (g/100 g total amino acids) |
|---|---|
| Phe | 3.2-.2 |
| Thr | 5.0-12.0 |
| Trp | 1.7-2.2 |
| Val | 5.5-7.0 |
| His | 1.8-2.3 |
| Arg | 2.3-7.0 |
| Pro | 5.0-6.0 |
| Gly | 1.9-3.2 |
| Ala | 1.5-5.1 |
| Ser | 5.0-16.0 |
| Tyr | 1.0-4.0 |
| Cys | 2.3-10.0 |
| Asp | 4.0-15.0 |
| Glu | 9.0-17.0 |
| Gln | 0-17.0 |
| Aromatics | 4.2-11.2 |
| Sulphur containing | 4.7-13.2 |
| BCAA | 22.0-28.0 |

More preferably the embodiment comprises all of the above amino acids in the amounts specified.

Preferably, an embodiment of the composition may be administered enterally. In an alternative embodiment it may be administered orally. Preferably, it is suitable for metabolically stressed patients; human and companion animal.

Preferably, an embodiment of the composition comprises free amino acids which provide about 15% to about 25% of the energy of the composition, more preferably about 20% of the energy of the composition.

Preferably, an embodiment of the composition comprises a carbohydrate source which provides about 40% to about 75% of the energy of the composition, more preferably about 65% to about 75% of the energy of the composition, most preferably about 70% of the energy of the composition. Preferably, the carbohydrate source comprises about 85% to about 95% maltodextrin, more preferably about 90% maltodextrin. Preferably, the carbohydrate source comprises about 5% to about 15%, more preferably about 10% low protein starch. Preferably, the low protein starch is low protein corn or potato starch.

Preferably, an embodiment of the composition comprises a lipid source which provides about 5% to about 40% of the energy of the composition, more preferably about 5% to about 15% energy of the composition, most preferably about 10% energy of the composition. Preferably the lipid source includes a mixture of medium and long chain triglycerides. Preferably the mixture comprises about 70% to about 80% long chain triglycerides, more preferably about 75%. Preferably the mixture comprises about 20% to about 30% medium chain triglycerides (MCT), more preferably about 25%. Preferably the mixture includes soybean oil and/or MCT.

Preferably, an embodiment of the composition has a caloric density of at least about 1.0 to about 1.4 kcal/ml.

Preferably, an embodiment of the composition has a maximum osmolarity (mOsm/kg water) of about 600 to about 900, more preferably about 650 to about 800, most preferably about 750 mOsm.

Preferably, an embodiment of the composition comprises vitamins and minerals.

Preferably, an embodiment of the composition is in ready-to-use form, is nutritionally complete, and contains free amino acids, carbohydrates, lipids, vitamins and minerals in proportions suitable for older children (10+years) and adults.

Preferably, an embodiment of the method according to the invention comprises the steps of blending the required free amino acids in the required amounts.

Preferably the method comprises the steps of mixing and pre-processing with oil and emulsifiers, homogenising, adding salts, standardising, adding the vitamin premix, sterilising and packing.

Preferably the packing is carried out with a sterile finished product under aseptic conditions into containers. The containers are exposed to super-heated steam prior to filling and the are filled and sealed in a sterile steam environment.

Additional features and advantages of the present invention are described in, and will be apparent from, the description of the presently preferred embodiments which are set out below.

Nutritional support of hospitalised as well as non-hospitalised patients requires prevention, recognition and treatment of nutritional depletion that may occur with illness. The goals of nutritional support include stabilising metabolic state, maintaining body mass, and/or facilitating growth in the presence of disease and gastrointestinal dysfunction.

Certain disease states exist that alter intake, absorption or metabolism. For example, certain health conditions can impair the nutrient absorption and/or reduced gastrointestinal tolerance for diets which are based on whole proteins. These conditions include patients suffering specifically from a compromised gut function as well as patients, due to the severity of their condition, who are simply unable to tolerate whole protein diets.

Patients transitioning from parenteral feeding, those that are acutely ill, or are considered post-surgery with cardiac/renal complications requiring fluid control have a need for nutrition, but often do not need or are unable to tolerate protein levels beyond normal requirements.

An embodiment of the composition preferably comprises medium chain triglycerides and maltodextrin which provide the advantage of enhancing absorption in patients.

An embodiment comprises free amino acids which provide approximately 20% of the total energy of the composition. In an embodiment, the amino acids comprise 20% (5 g/100 kcal) of the total energy of the composition. For adults and older children (10+ years old), the free amino acid concentration is optimal for the moderate tissue repair needs of the targeted patient populations without imposing an undue nitrogen burden on renal function.

An embodiment is based on free amino acids which provides the advantage of maximising tolerance and absorption.

A preferred embodiment comprises the amino acid cysteine. This is advantageous because cysteine is a limiting amino acid for the formation of glutathione, and endogenous glutathione needs are greater in patients with chronic inflammatory and infectious conditions. The composition preferably contains approximately 2.3 g to about 10.0 g of cysteine per 100 g free amino acids. In a preferred embodiment, the composition contains approximately 3.0 g cysteine per 100 g free amino acids.

In an embodiment, the carbohydrate source provides about 70% of the energy of the composition. A number of carbohydrates may be used. By way of example, the carbohydrates can be chosen from maltodextrin, corn starch, sucrose, lactose, glucose, fructose, corn syrup solids or a mixture thereof.

The lipid source may include a mixture of medium chain triglycerides (MCT) and long chain triglycerides (LCT). The lipid source provides about 10% of the energy of the composition.

The lipid profile is designed to meet essential fatty acid needs (omega-3 and omega-6) while also keeping the medium-chain triglyceride (MCT) content high and long-chain triglyceride (LCT) content low compared with prior formulas. Preferably, the lipid source comprises approximately 20% to 30% by weight MCTs. In a preferred embodiment, the lipid source includes about 25% by weight from MCTs. MCTs provide the advantage that they are easily absorbed and metabolised in a metabolically stressed patient. The use of MCTs reduces the risk of nutrient malabsorption. In a preferred embodiment, the medium chain triglyceride source is fractionated coconut oil.

The remainder of the lipid source is a mixture of LCTs. A suitable source of LCTs is canola oil, corn oil, soy lecithin, residual milk fat, soybean oil or a mixture thereof. The lipid profiles containing such LCTs are designed to have a polyunsaturated fatty acid omega-6 (n–6) to omega-3 (n–3) ratio of about 1:1 to 10:1; preferably about 6:1 to about 9:1. The proposed ratio of n–6:n–3 is designed to reduce the immune suppression associated with high omega-6 fatty acid concentration and provide adequate essential fatty acid. In an embodiment, the composition includes an omega-6 to omega-3 ratio of about 7:1.

An embodiment comprises a specialised vitamin and mineral profile. Moreover, the composition includes higher levels of key vitamins and minerals designed to support metabolically stressed patients. Specifically, the composition may include one or more of the following vitamins and minerals in about the following amounts.

| Amino Acids | Amount (g/100 g total amino acids) |
|---|---|
| Vitamin A (IU) | 3300 |
| Beta-Carotene (mg) | 1 |
| Vitamin D (IU) | 400 |
| Vitamin E (IU) | 30 |
| Vitamin K1 (µg) | 50 |
| Vitamin C (mg) | 340 |
| Vitamin B1 (mg) | 2.0 |
| Vitamin B2 (mg) | 2.4 |
| Niacin (mg) | 28 |
| Vitamin B6 (mg) | 4.0 |
| Folic Acid (µg) | 540 |
| Pantothenic Acid (mg) | 14 |
| Vitamin B12 (µg) | 8.0 |
| Biotin (µg) | 400 |
| Choline (mg) | 450 |
| Taurine (mg) | 100 |
| Carnitine (mg) | 100 |
| Sodium (mg) | 560 |
| Potassium (mg) | 1500 |
| Chloride (mg) | 1000 |
| Calcium (mg) | 800 |
| Phosphorus (mg) | 700 |
| Magnesium (mg) | 297 |
| Manganese (µg) | 2700 |
| Iron (mg) | 18 |
| Iodine (µg) | 150 |
| Copper (mg) | 2.0 |
| Zinc (mg) | 24 |
| Selenium (µg) | 50 |
| Chromium (µg) | 40 |
| Molybdenum (µg) | 120 |

A preferred embodiment comprises all of the above vitamins and minerals in the specified amounts.

Preferably, zinc is provided in the composition because it has the advantage that it compensates for zinc losses and provides increased zinc for tissue repair in a patient having increased healing requirements.

The composition includes vitamin C which provides the advantage that it accelerates healing and granulation in patients with severe healing requirements. In an embodiment, 340 mg vitamin C is provided per 1000 kcal. Vitamin C supports increased requirements/losses after surgery.

The composition may include increased amounts of selenium compared to known formulae. Selenium deficiencies may develop in patients having elevated healing requirements. At least about 60 to about 90 μg of selenium may be provided in 1000 kcal of composition. In a preferred embodiment, approximately 50 μg of selenium per 1000 calories is provided.

Many of the commercially available enteral formulas contain far below the amount of carotenoids (beta-carotene) found in usual diets of normal healthy people. In fact, patients on liquid formula diets as their sole source of nutrition for one week or more have been found to have plasma concentrations of carotenoids of only 8% to 18% as compared to controls consuming a free choice of diet (Bowen et al, "Hypocarotenemia in Patients Fed Enterally with Commercial Liquid Diets," Journal of Parenteral and Enteral Nutrition, 12(5): 4449 (1988)). Those on enteral formulas for more than three weeks have negligible concentrations of any common serum carotenoids.

To meet these requirements, the composition may include a source of β-carotene. β-Carotene is added to the composition to normalise beta-carotene serum plasma levels and to avoid beta-carotene deficiency in long term tube-fed patients. β-Carotene also meets a portion of the required Vitamin A, thereby meeting micro-nutrient requirements in a small caloric volume. Moreover, β-carotene is an important nutrient with anti-oxidant properties. In a preferred embodiment, the composition includes approximately 1.0 mg of β-carotene per 1000 kcal of the composition. This amount prevents deficiencies and provides for possible increased requirements in the healing patient. Moreover, the β-carotene and vitamin A levels allow plasma concentrations of retinol to be increased to near normal optimal levels of 500 mcg per litre.

The composition may include L-carnitine and taurine to support the increased requirements of the acutely ill, catabolic patient. In preferred embodiments, both taurine and L-carnitine are present in an amount of approximately 100 mg per 1000 kcal.

An embodiment may include decreased amounts of magnesium. Magnesium has been associated with diarrhoea. In a preferred embodiment, magnesium is present in an amount of approximately 297 mg per 1000 kcal.

A preferred embodiment of the composition can provide the total nutritional requirements of the metabolically stressed patient or can act as a supplement. The composition can be tube-fed to a patient, or fed by having the patient drink it. For instance, the composition can be provided in cans or a spike and hang bag. The composition is preferably ready-to-use and does not require reconstitution or mixing prior to use.

A preferred embodiment of the composition has a caloric density of about 1.0 kcal/ml.

The composition may be used in the prevention or treatment of patients having impaired gastro-intestinal tract function. These patients may be unable to tolerate whole protein diets, but still require nutrition. For example, the composition may be utilised to provide nutrition to critically ill patients transitioning from total parenteral nutrition therapy and acutely ill, catabolic patients. Moreover, the composition can be utilised to provide nutrition to patients suffering from the following conditions and/or diseases; Crohn's disease; cystic fibrosis; HIV/AIDS; cancer; patients of post-surgery with cardiac/renal complications requiring fluid control; intractable diarrhoea; short bowel syndrome; cerebral palsy; and gastric reflux.

Of course, it will be appreciated that a variety of compositions are possible. An example of a composition has a caloric density of about 1.5 kcal/ml. This is equivalent to 375 kcal/250 ml which will, in a preferred embodiment, be one unit (can or container) of product.

This embodiment of the composition described is ready to use for enteral administration.

The following examples are given by way of illustration only and in no way should be construed as limiting the subject matter of the present application.

EXAMPLE 1

Nutritional Composition

A ready to use unflavoured composition in liquid form was prepared for tube or oral use. The composition comprised the constituents indicated below:

| Product | Ready to use composition having free amino acids |
|---|---|
| Energy Density (kcal/ml) | 1.0 |
| Protein Equivalent (% of kcal) | 20 |
| Carbohydrate (%/kcal) | 70 |
| Fat (% kcal) | 10 |
| Flavour | unflavoured |
| Minerals and vitamins | As required |
| Amino acids (all shown as g/100 g total amino acids | |
| Ile | 6.5 |
| Leu | 13.0 |
| Lys | 7.0 |
| Met | 3.0 |
| Phe | 7.0 |
| Thr | 7.0 |
| Trp | 2.0 |
| Val | 6.5 |
| His | 2.0 |
| Arg | 6.0 |
| Pro | 5.0 |
| Gly | 2.0 |
| Ala | 3.0 |
| Ser | 5.0 |
| Tyr | 1.5 |
| Cys | 2.5 |
| Asp | 4.0 |
| Glu | 17.0 |
| Gln | 0 |

EXAMPLE 2

Nutritional Composition

A ready to use unflavoured composition in liquid form was prepared for tube or oral use. The composition comprised the constituents indicated below:

| Product | Ready to use composition having free amino acids |
|---|---|
| Energy Density (kcal/ml) | 1.0 |
| Protein Equivalent (% of kcal) | 20 |
| Carbohydrate (%/kcal) | 70 |
| Fat (% kcal) | 10 |
| Flavour | unflavoured |
| Minerals and vitamins | As required |
| Amino acids (all shown as | |

-continued

| Product | Ready to use composition having free amino acids |
|---|---|
| g/100 g total amino acids | |
| Ile | 6.5 |
| Leu | 13.0 |
| Lys | 7.0 |
| Met | 2.4 |
| Phe | 4.9 |
| Thr | 7.0 |
| Trp | 2.0 |
| Val | 6.5 |
| His | 2.0 |
| Arg | 3.0 |
| Pro | 5.0 |
| Gly | 2.0 |
| Ala | 1.5 |
| Ser | 6.0 |
| Tyr | 1.0 |
| Cys | 3.0 |
| Asp | 10.9 |
| Glu | 17.0 |
| Gln | 0 |

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of providing nutrition to an individual having impaired gastro-intestinal tract function, the method comprising:
   administering to an individual having impaired gastro-intestinal tract function a therapeutically effective amount of a composition comprising free amino acids and 9.0% to about 17.0% glutamic acid by weight of total amino acids of the composition, wherein the composition has no glutamine, and wherein the composition comprises methionine in an amount from about 2.4 to about 3.2 g/100 g total amino acids.

2. The method according to claim 1, wherein the composition comprises cysteine in an amount from about 2.3 to about 10 g.

3. The method according to claim 1, wherein the impaired gastro-intestinal function is due to Crohn's disease, cystic fibrosis, HIV/AIDS, cancer, post surgery complications, intractable diarrhoea, short bowel syndrome, cerebral palsy or gastric reflux.

4. The method according to claim 1, wherein the composition is in a ready to use form.

5. The method according to claim 1, wherein the composition comprises arginine in an amount from 2.3% to 7% total amino acids by weight.

6. The method according to claim 1, wherein the composition comprises aspartic acid.

7. The method according to claim 1, wherein the composition comprises leucine.

8. The method according to claim 1, wherein the composition comprises threonine.

9. The method according to claim 1, wherein the composition comprises proline.

10. The method according to claim 1, wherein the composition comprises tryptophan.

11. The method according to claim 1, wherein the composition comprises serine.

12. The method of claim 1, wherein the composition comprises lysine.

13. The method of claim 1, wherein the composition comprises branched amino acids.

14. The method of claim 1, wherein the composition further comprises at least one amino acid in the following amounts selected from the group consisting of:

| Amino Acids | Amount (g/100 g total amino acids) |
|---|---|
| Ile | 5.7-7.0 |
| Leu | 10.8-14.0 |
| Lys | 6.5-10.0 |
| Phe | 3.2-.2 |
| Thr | 5.0-12.0 |
| Trp | 1.7-2.2 |
| Val | 5.5-7.0 |
| His | 1.8-2.3 |
| Arg | 2.3-7.0 |
| Pro | 5.0-6.0 |
| Gly | 1.9-3.2 |
| Ala | 1.5-5.1 |
| Ser | 5.0-16.0 |
| Tyr | 1.0-4.0 |
| Cys | 2.3-10.0 |
| Asp | 4.0-15.0 |
| Aromatics | 4.2-11.2 |
| Sulphur containing | 4.7-13.2 |
| BCAA | 22.0-28.0. |

15. The method of claim 1, wherein the composition comprises:

| Amino Acids | Amount (g/100 g total amino acids) |
|---|---|
| Ile | 5.7-7.0 |
| Leu | 10.8-14.0 |
| Lys | 6.5-10.0 |
| Met | 2.4-3.2 |
| Phe | 3.2-.2 |
| Thr | 5.0-12.0 |
| Trp | 1.7-2.2 |
| Val | 5.5-7.0 |
| His | 1.8-2.3 |
| Arg | 2.3-7.0 |
| Pro | 5.0-6.0 |
| Gly | 1.9-3.2 |
| Ala | 1.5-5.1 |
| Ser | 5.0-16.0 |
| Tyr | 1.0-4.0 |
| Cys | 2.3-10.0 |
| Asp | 4.0-15.0 |
| Glu | 9.0-17.0 |
| Aromatics | 4.2-11.2 |
| Sulphur containing | 4.7-13.2 |
| BCAA | 22.0-28.0. |

\* \* \* \* \*